United States Patent [19]

Iimuro et al.

[11] Patent Number: 4,931,146

[45] Date of Patent: Jun. 5, 1990

[54] PROCESS FOR OBTAINING HIGH-PURITY BISPHENOL A

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 329,867

[22] Filed: Mar. 28, 1989

[30] Foreign Application Priority Data

Apr. 5, 1988 [JP] Japan ................................ 63-83905

[51] Int. Cl.$^5$ .......................... B01D 3/04; B01D 3/10
[52] U.S. Cl. ....................... 203/92; 203/96; 568/724
[58] Field of Search ................ 203/91, 92, 95–96; 202/205, 237; 159/26.1, DIG. 16, DIG. 10; 568/724

[56] References Cited

U.S. PATENT DOCUMENTS

| | | | |
|---|---|---|---|
| 2,609,334 | 9/1952 | Pyle et al. | 202/237 |
| 2,730,553 | 10/1956 | Williamson | 568/528 |
| 3,073,868 | 1/1963 | Prahl et al. | 568/724 |
| 3,936,507 | 2/1976 | Ligorati et al. | 568/724 |
| 3,972,950 | 8/1976 | Kwantes | 568/724 |
| 4,160,110 | 7/1979 | Carnahan, Jr. | 203/6 |
| 4,400,553 | 8/1983 | Aneja | 568/724 |
| 4,408,087 | 10/1983 | Li | 568/724 |
| 4,447,655 | 5/1984 | Mendiratta | 568/724 |
| 4,504,364 | 3/1985 | Chen | 203/96 |
| 4,507,509 | 3/1985 | Mendiratta et al. | 568/724 |
| 4,798,654 | 1/1989 | Iimuro et al. | 568/724 |

FOREIGN PATENT DOCUMENTS

| | | |
|---|---|---|
| 0123210 | 10/1984 | European Pat. Off. |
| 40-7186 | 2/1962 | Japan |
| 47-43937 | 11/1972 | Japan |
| 57-88137 | 6/1982 | Japan |

OTHER PUBLICATIONS

Chemical Abstracts, vol. 109, No. 18, Abstract No. 150239t, Oct. 31, 1988.

*Primary Examiner*—Virginia Manoharan
*Attorney, Agent, or Firm*—Burns, Doane, Swecker & Mathis

[57] ABSTRACT

A process for obtaining high-purity bisphenol A by removing most part of phenol from an adduct of bisphenol A with phenol and removing continously the residual phenol by steam stripping, wherein a multi-tubular packed column is used as a stripping equipment. The residual phenol in bisphenol A can be removed constantly. In addition, the process of the present invention is economical because the residual phenol can be removed with a small amount of steam.

3 Claims, No Drawings

PROCESS FOR OBTAINING HIGH-PURITY BISPHENOL A

BACKGROUND OF THE INVENTION

The present invention relates to a process for obtaining high-purity bisphenol A and, more particularly, it relates to a process for removing phenol in bisphenol A effectively and constantly through a special steam stripping process.

Bisphenol A is used as a raw material for polycarbonate resins. However, since phenol contained in bisphenol A acts as a terminal-group capping agent in polycarbonate resins, it has been desired to remove completely phenol in bisphenol A.

One of the processes for obtaining bisphenol A consists of reacting phenol with acetone from the presence of an acid catalyst, removing the catalyst, water, unreacted acetone and a small amount of phenol from the product mixture, cooling the residual liquid mixture to crystallize bisphenol A as an adduct with phenol, separating the adduct from the mother liquor, and removing phenol from the adduct to obtain bisphenol A.

A known method for removing phenol from the adduct of bisphenol A with phenol comprises distilling off phenol under reduced pressure. However, phenol cannot be removed completely with this method. Accordingly, it is necessary to use another step such as steam stripping as described in Japanese Patent Publication No. 43937/1972 or No. 7186/1965, or recrystallization from a hot aqueous solution as disclosed in Japanese Patent Laid-Open No. 88137/1982.

So as to remove phenol industrially by steam stripping, a packed column or a wetted-wall column is used, and bisphenol A containing phenol is introduced at the top while superheated steam is supplied at the bottom to contact the material in counterflow.

When a packed column is used, a deflected flow occurs in the column as the diameter of the column increases and therefore the contact between gas and liquid becomes uneven and thus a large amount of phenol remains in the thus-obtained bisphenol A.

In addition, since the melting point of bisphenol A is high and reaches about 157° C., bisphenol A is apt to solidify in the packed column and block it even if the packed column is heated as a whole.

When a wetted-wall column is used, there occurs no abovementioned trouble. However, so as to enlarge its throughput capacity, it is necessary to increase the diameter and the length of the column because the contact area between gas and liquid is small.

Furthermore, in both cases, there is needed an enormous amount of steam in order to remove phenol completely and, in these cases, a post treatment is necessary. Therefore, the abovementioned methods for removing phenol are not economical.

SUMMARY OF THE INVENTION

It is an object of the present invention to provide a process for removing a small amount of phenol contained in bisphenol A by steam stripping, wherein phenol can be removed effectively and the process is stable.

As a result of our extensive studies, we found that the above-mentioned object is achieved by using a multi-tubular packed column as a stripping equipment. The present invention was completed on the basis of this finding.

In accordance with the present invention, there is provided a process for obtaining high-purity bisphenol A by removing a major portion of phenol from an adduct of bisphenol A with phenol and removing continuously the residual phenol by steam stripping, wherein a multi-tubular packed column is used as a stripping equipment.

DETAILED DESCRIPTION OF THE INVENTION

The adduct of bisphenol A with phenol to be treated in the present invention may be obtained by reacting phenol with acetone in the presence of an acid catalyst, removing the catalyst, water, unreacted acetone and a small amount of phenol from the product mixture, cooling the residual liquid mixture to crystalline bisphenol A as an adduct with phenol, separating the adduct from the mother liquor, and removing phenol from the adduct to obtain bisphenol A, or by dissolving crude bisphenol A in phenol, cooling the resulting liquid mixture to crystallize an adduct of bisphenol A with phenol, and separating the adduct from the mother liquor.

In the present invention, the removal of the major portion of phenol from the adduct of bisphenol A with phenol can be accomplished with a variety of known processes such as distillation, extraction, steam stripping and so on. At this stage, it is preferable to remove phenol from the adduct so that the weight ratio of phenol to bisphenol A becomes from 0.01:1 to 0.1:1.

The multi-tubular packed column to be used in the present invention is a multi-tubular wetted-wall column whose wetted-wall inner tubes are packed with a packing such as Raschig rings and it is preferable that each inner tube can be heated from the exterior thereof. The inner diameter of the inner tube can vary according to the throughput rate of the packed column and is preferably 0.5 to 5.0 inches. The length of the inner tube is preferably 1 to 10 meters. Various sizes of packings can be used according to the diameter of the tube, throughput rate and the shape of the packing. The weight ratio of steam to bisphenol A introduced into the multi-tubular packed column is preferably from 0.01:1 to 1.1. The optimum conditions for stripping in the multi-tubular packed column are from 160° to 200° C. in temperature and from 20 to 400 Torr in pressure.

EXAMPLES

The present invention will be described in more detail with reference to the following examples.

In the examples, "%" means "wt%" unless otherwise indicated.

EXAMPLE 1

A product mixture was obtained by condensing phenol with acetone in the presence of a hydrochloric acid catalyst. The product mixture was composed of 59.3% of phenol, 32% of bisphenol A, 2% of by-products, 4% of water and 2.7% of hydrogen chloride.

This product mixture was transferred to a dehydrochlorination tower and the tower was operated at 70 Torr and with its bottom temperature at 120° C. Water, hydrochloric acid and a small amount of phenol were removed in the tower.

The product mixture obtained from the bottom of the tower was cooled and an adduct of bisphenol A with phenol was crystallized at 45° C. The crystallized adduct was separated from the mother liquor by using a separator.

This separated adduct was transferred to a phenol stripping tower and the tower was operated at 50 Torr and with its bottom temperature at 180° C. After the removal of phenol in the tower, the concentration of phenol in bisphenol A at the bottom was 3%.

The bisphenol A was then transferred to a stripping tower at a flow rate of 250 kg/hr.

The stripping tower was a multi-tubular packed column equipped with ten wetted-wall tubes having a inner diameter of 69 mm and a length of 6,000 mm and these tubes were packed respectively with half-inch Raschig rings. The stripping tower was operated at 75 Torr and 190° C.

Superheated steam at 180° C. was blown into the supplied bisphenol A with a ratio of 3% to the supplied bisphenol A and the concentration of phenol in the bisphenol A discharged from the bottom of the tower was 0.001%.

COMPARATIVE EXAMPLE 1

Bisphenol A was obtained through the treatment as described in Example 1 except for the above stripping operation.

The stripping tower used in this comparative example was the same multi-tubular wetted-wall column used in Example 1 except that the packing was removed from the multi-tubular packed column. The stripping tower was operated at 75 Torr and 190° C.

Even when superheated steam at 180° C. was blown into the supplied bisphenol A with the ratio of 10% to the bisphenol A supplied at the flow rate of 250 kg/hr, the concentration of phenol in the bisphenol A discharged from the bottom of the tower was high and reached 0.010%.

COMPARATIVE EXAMPLE 2

Bisphenol A was obtained through the treatment as described in Example 1 except for the above stripping operation.

The stripping tower used in this comparative example was a packed column having an inner diameter of 211 mm and a length of 6,000 mm and the equipped tubes were packed with half-inch Raschig rings. The stripping tower was operated at 75 Torr and 190° C.

Even when superheated steam at 180° C. was blown into the supplied bisphenol A with the ratio of 10% to the bisphenol A supplied at the flow rate of 250 kg/hr, the concentration of phenol in the bisphenol A discharged from the bottom of the tower varied between 0.020 and 0.040%.

According to the process of the present invention, the residual phenol in bisphenol A can be removed constantly.

In addition, the process of the present invention is economical because the residual phenol can be removed with a small amount of steam.

What is claimed is:

1. A process for obtaining high-purity bisphenol A which comprises removing a major portion of phenol from an adduct of bisphenol A with phenol so that the weight ratio of phenol to bisphenol A is from 0.01:1 to 0.1:1 and then removing continuously the residual phenol by steam stripping in a multi-tubular packed column wherein the bisphenol A and steam are supplied to the interior of a plurality of packed tubes wherein the weight ratio of steam to bisphenol A is 0.01:1 to 1:1 so that the concentration of phenol in the high purity bisphenol A is less than about 0.01% by weight.

2. A process as claimed in claim 1, wherein each tube of the multi-tubular packed column is heated from the exterior thereof.

3. A process as claimed in claim 1, wherein the multi-tubular packed column is operated at a temperature of 160° to 200° C. and at a pressure of 20 to 400 Torrs.

* * * * *